United States Patent [19]

Ito

[11] Patent Number: 5,128,304
[45] Date of Patent: Jul. 7, 1992

[54] CATALYST FOR ALKYLATION OF PHENOLS

[75] Inventor: Muneo Ito, Tsukuba, Japan

[73] Assignee: Mitsubishi Gas Chemical Co., Inc., Tokyo, Japan

[21] Appl. No.: 736,066

[22] Filed: Jul. 25, 1991

Related U.S. Application Data

[62] Division of Ser. No. 570,327, Aug. 21, 1990.

[30] Foreign Application Priority Data

Aug. 22, 1989 [JP] Japan ................... 1-214059

[51] Int. Cl.$^5$ ................... B01J 21/08; B01J 23/78
[52] U.S. Cl. ................... 502/242
[58] Field of Search ................... 502/242

[56] References Cited

U.S. PATENT DOCUMENTS

| 3,953,529 | 4/1976 | Yonemitsu et al. | 568/804 |
| 4,329,517 | 5/1982 | Taniguchi et al. | 502/182 X |
| 4,359,591 | 11/1982 | Fremery et al. | 568/804 |
| 4,400,557 | 8/1983 | Fremery et al. | 568/804 |
| 4,406,824 | 9/1983 | Fremery et al. | 502/256 |
| 4,424,141 | 1/1984 | Grasselli et al. | 502/242 X |
| 4,429,171 | 1/1984 | Sakurai et al. | 568/804 |
| 4,556,731 | 12/1985 | Guttmann et al. | 502/242 X |
| 4,590,306 | 5/1986 | Korff et al. | 568/804 |

FOREIGN PATENT DOCUMENTS

0019476  5/1980  European Pat. Off. .
5728018  7/1980  Japan .

*Primary Examiner*—W. J. Shine
*Assistant Examiner*—Douglas J. McGinty
*Attorney, Agent, or Firm*—Sherman and Shalloway

[57] ABSTRACT

A method of alkylating phenols which comprises reacting phenols having a hydrogen atom in at least one of the ortho-positions with regard to the hydroxyl group with an alcohol in a gaseous phase under heat in the presence of a catalyst comprising iron oxide, silica, chromium oxide, germanium oxide and an alkali metal compound. The catalyst exhibits a long catalytic activity duration and decreases frequency of regeneration and replacement of catalysts.

3 Claims, No Drawings

CATALYST FOR ALKYLATION OF PHENOLS

This is a division of application Ser. No. 07/570,327, filed Aug. 21, 1990.

DETAILED DESCRIPTION OF THE INVENTION

This invention relates to a method of alkylation of phenols and to a catalyst therefor. More specifically, it relates to a method of selective alkylation of phenols in the ortho-position and to a catalyst therefor.

Phenols alkylated in the ortho-position are useful as an industrial material for a variety of products. For example, 2,6-xylenol is used as a material for a polyphenylene oxide resin, and 2,3,6-trimethylphenol as a material for vitamin E.

A method for producing ortho-alkylated phenols has been known, in which a phenol compound and an alcohol are allowed to catalytically react with each other in a gaseous phase to alkylate the phenol compound in the ortho-position.

U.K. Patent 717,588 discloses a method using, as a catalyst, a metal oxide, preferably aluminum oxide.

Japanese Patent Publication No. 6894/1967 discloses a method using, as a catalyst, magnesium oxide.

Japanese Patent Publication No. 11101/1966 discloses a method using, as a catalyst, manganese oxide.

Further, Japanese Patent Publication No. 51367/1982 discloses a method using, as a catalyst, chromium oxide.

However, the aluminum oxide catalyst is not satisfactory in view of activity and alkylation selectivity to the ortho-position. The magnesium oxide catalyst does not exhibit sufficient activity although it has comparatively high selectivity to the ortho-position. That is, the magnesium oxide catalyst requires a very high reaction temperature of 475° to 600° C., and hence, is disadvantageous in regard to energy. It also needs to be improved in activity duration. Further, the manganese oxide catalyst and chromium oxide catalyst show poor activity duration and a sharp decline in activity with the progress of reaction, although they have comparatively high activity and selectivity.

The present inventor therefore has made a diligent study to develop a catalyst system which exhibits high activity at an energy saving advantageous low temperature, and which has a long activity duration time and excellent selectivity to the ortho position. As a result, the following catalysts have been found, and already proposed.

That is, U.S. Pat. No. 3,953,529 (see corresponding Japanese Patent Publications Nos. 12689/1977 and 12690/1977) discloses a method of alkylating phenols in the ortho-position by reacting the phenols with an alcohol in the presence, as a catalyst, of:

a. a mixture of iron oxide and silica, or b. a mixture of iron oxide, silica and chromium oxide.

U.S. Pat. No. 4,024,195 (see corresponding Japanese Patent Publication No. 12692/1977) discloses a method of alkylating phenols by reacting the phenols with an alcohol in the presence, as a catalyst, of a mixture of iron oxide, silica, chromium oxide and an alkyl metal compound.

Of the above catalysts proposed by the present inventor, in particular, the mixture of iron oxide, silica, chromium oxide and an alkali metal compound is a catalyst which exhibits a much longer activity duration time than the conventional catalysts, while maintaining high selectivity to the ortho-position. However, the catalyst activity decreases since a carbonaceous substance is deposited on the catalyst and the catalyst is gradually sintered with a lapse of reaction time. Hence, when the above catalyst is industrially used, the following remains to be solved: periodic catalyst regeneration operation to remove the deposited carbonaceous substance and replacement of catalysts used for a certain period are required.

It is an object of this invention, therefore, to provide a method of alkylating phenols in the presence of an alkylating catalyst having a novel composition.

It is another object of this invention to provide a method of alkylating phenols in the presence of an alkylating catalyst having a longer activity duration than conventional catalysts.

It is still another object of this invention to provide a method of alkylating phenols in the presence of an alkylating catalyst which is capable of reducing frequency of regeneration and replacement of catalysts as compared with conventional catalysts.

It is further another object of this invention to provide a method of alkylating phenols which is industrially advantageous in many points including achievement of the above objects and advantages.

Further, it is another object of this invention to provide the above-described catalyst and use thereof.

The other objects and advantages of this invention will be apparent from the following description.

According to this invention, the above objects and advantages of this invention are achieved, in the first place, by a method of alkylating phenols which comprises reacting phenols having a hydrogen atom in at least one of the ortho-positions with regard to the hydroxyl group with an alcohol in a gaseous phase under heat in the presence of a catalyst comprising iron oxide, silica, chromium oxide, and alkali metal compound and germanium oxide.

Phenols used as a material in this invention have a hydrogen atom in at least one of the ortho-positions.

Preferred examples of such phenols are compounds represented by the following formula (I).

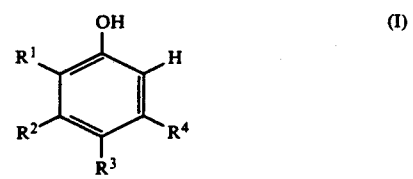

wherein $R^1$, $R^2$, $R^3$ and $R^4$ may be identical to or different from each other and each represents a hydrogen atom, an alkyl group, a cycloalkyl group, an aryl group or an alkylaryl group.

In the above formula (I), as an alkyl group, alkyl groups having 1 to 6 carbon atoms are preferred, and the alkyl groups may be linear or branched. Examples of such alkyl groups are methyl, ethyl, n-propyl, isopropyl, n-butyl, n-pentyl, and n-hexyl groups. As a cycloalkyl group, preferred examples are cyclopentyl and cyclohexyl groups. As an aryl group, preferred examples are phenyl and naphthyl groups. As an alkylaryl group, preferred examples are phenyl and naphthyl groups which are substituted with an alkyl group having 1 to 6 carbon atoms.

In the above formula (I), $R^1$, $R^2$, $R^3$ and $R^4$ may be the same as, or different from, the other.

Examples of the phenols of the above formula (I) are phenol, o-cresol, m-cresol, p-cresol, 2,3-xylenol, 2,4-xylenol, 2,5-xylenol, 3,5-xylenol, 3,4-xylenol, 2,3,4-trimethylphenol, 2,3,5-trimethylphenol, 2,4,5-trimethylphenol, 2,3,4,5-tetramethylphenol, o-ethylphenol, m-ethylphenol, p-ethylphenol, 2,3-diethylphenol, 2,4-diethylphenol, 2,5-diethylphenol, 3,5-diethylphenol, 3,4-diethylphenol, 2,3,4-triethylphenol, 2,3,5-triethylphenol, 2,4,5triethylphenol, o-propylphenol, o-phenylphenol, p-phenylphenol, o-cyclohexylphenol, p-cyclohexylphenol, and the like.

As an alcohol used as the other material in this invention, lower saturated aliphatic alcohols having 1 to 4 carbon atoms are preferred. These alcohols may be linear or branched. Examples of such alcohols are methanol, ethanol, n-propanol, iso-propanol, n-butanol, iso-butanol, and the like. Of these, methanol and ethanol are preferred, and methanol is particularly preferred.

The catalyst used in this invention comprises iron oxide, silica, chromium oxide, an alkali metal compound and germanium oxide.

This catalyst can maintain high catalyst activity for a long period of time and achieve alkylation of phenols with high selectivity to the orthoposition and at high yields as compared with conventional catalysts. Moreover, the catalyst of this invention ("present catalyst" hereinafter) makes it possible to proceed with the reaction at a lower temperature as compared with conventional catalysts, whereby it is possible to prevent deposition of a carbonaceous substance on the catalyst and sintering of the catalyst which are causes for deterioration of catalyst activity. Therefore, duration of catalyst activity can be further improved, and frequency of catalyst regeneration and replacement can be decreased.

The above composition of the present catalyst is novel as a catalyst for ortho-alkylation of phenols with an alcohol.

The present catalyst contains iron oxide, silica, chromium oxide, germanium oxide and an alkali metal compound in a Fe:Si:Cr:Ge:alkali metal atomic ratio preferably of 100:0.1-20:0.1-5:0.1-10:0.01-5, more preferably of 100:0.1-5:0.1-3:0.1-5:0.01-1.

The present catalyst can be produced according to various known methods. For example, at first, a mixture of an iron compound, a silicon compound, a chromium compound and a germanium compound is prepared by a) a co-precipitation method, b) a kneading method or c) a combination of a co-precipitation method and a kneading method. When the mixture is calcined, the metal compounds in the mixture become corresponding metal oxides. Then, an alkali metal compound is allowed to be deposited for in the mixture, and calcined. The deposition is carried out by a') an impregnation method, b') a kneading method or c') an evaporation and dry-solidification method. The impregnation method is generally used.

The method for preparation of the present catalyst will be further specifically explained below.

While an aqueous solution of a mixture of predetermined amounts of iron, silicon and chromium compounds is stirred at a temperature between 10° C. and 100° C., an alkali agent is added to the solution to adjust the solution to pH of 6 to 9, whereby a precipitate is obtained. Then, the predetermined amount of a germanium compound is added to the precipitate, and the resultant mixture is further continuously stirred. Then, the resultant precipitate is fully washed with water and filtered to obtain a mixture of the iron compound, the silicon compound, the chromium compound and the germanium compound. This mixture is then dried at 100° to 350° C., and immersed in an aqueous solution of an alkali metal compound, and the mixture is filtered. Thereafter, the resultant solid is dried at 100° to 200° C., and then calcined in a stream of air at 400° to 600° C. for 3 to 15 hours.

Examples of the iron compound used for the preparation of the present catalyst are ferric nitrate, ferric sulfate, ferric chloride, ferrous nitrate, ferrous sulfate and ferrous chloride. Of these, ferric nitrate is particularly preferred. Examples of the silicon compound are sodium silicate, silica sol (colloidal silica) and organosilicon compounds. Examples of the chromium compound are trivalent chromium salts such as chromium nitrate, chromium sulfate and chromium chloride; chromates; and perchromates. Examples of the germanium compound are germanium tetrachloride, germanium oxide and organogermanium compounds. Examples of the alkali metal compound are nitrates, sulfates, carbonates or hydroxides of lithium, sodium, potassium, rubidium or cesium. Of these, a nitrate, sulfate or carbonate of potassium or lithium is particularly preferred. Presence of halogen such as chloride is undesirable.

An alkaline substance is used as a pH regulator in the preparation of the mixture of an iron compound, a silicon compound, a chromium compound and a germanium compound. Examples of such an alkaline substance are ammonia, urea and hydroxides of alkali metals, such as sodium hydroxide. Of these, ammonia is particularly preferred.

In this invention, both phenols and an alcohol are fed to a reaction system as gaseous substances, preferably in a phenols/alcohol molar ratio of 1:1-10. These gases to be fed may contain steam and inert gases such as nitrogen, etc., as a diluent, and steam is particularly preferred, since steam has effects of preventing decomposition of the alcohol, which improves the recovery ratio of the alcohol, and of preventing deposition of a carbonaceous substance on the catalyst. The steam is contained in an amount of 0.5 to 5 mols per mol of the phenols. The reaction temperature is preferably between 300° C. and 450° C., more preferably between 300° C. and 400° C. The reaction pressure may be ordinary pressure, elevated pressure or reduced pressure. When an elevated pressure is employed, a gage pressure of 0.5–40 kg/cm$^2$ is chosen.

After the reaction, the reaction product is condensed, or subjected to absorption with an organic solvent and separated by distillation, etc., whereby an intended product is obtained.

According to this invention, the above alkylation method of this invention can give a product mainly containing corresponding ortho-alkylated phenols. According to this invention, therefore, there is also provided a method of producing an ortho-alkylated phenol.

The present catalyst maintains high catalyst activity for a long period of time and exhibits high selectivity to the ortho-position as compared with conventional catalysts, whereby intended ortho-alkylation products can be obtained at high yields. Furthermore, since the present catalyst permits a reaction at a low temperature as compared with conventional catalysts, deposition of a carbonaceous substance on the catalyst and sintering of the catalyst are prevented, and as a result, durability of the catalyst activity is further improved. For these reasons, frequency of regeneration and replacement of catalysts can be decreased, and the present catalyst is industrially significant to a great extent.

This invention will be explained further in detail by reference to Examples, in which reaction results were defined by the following equations.

Phenol reaction ratio = [amount of phenol fed (mol) − amount of phenol unreacted (mol)]/amount of phenol fed (mol) × 100

Yield of component of product = amount of component produced (mol)/amount of phenol fed (mol) × 100

Selectivity to o-position (mol %) = [amount of 2,6-xylenol produced (mol) + amount of o-cresol produced (mol)]/[amount of phenol fed (mol) − amount of phenol unreacted (mol)] × 100

Methanol recovery ratio (%) = [amount of methanol recovered (mol)]/[amount of methanol fed (mol) − (amount of 2,6-xylenol produced × 2 + amount of o-cresol produced)] (mol) × 100

20 hours, and then, the precipitate was further dried at 350° C. for 5 hours. The resultant product was immersed in 2,024 g of an aqueous solution containing 3.74 g of potassium carbonate for 16 hours, and filtered, dried at 120° C. for 3 hours, and calcined in a stream of air at 470° C. for 7 hours to obtain a catalyst. The catalyst had a $Fe_2O_3:SiO_2:Cr_2O_3:GeO_2:K_2CO_3$ composition of 100:2:1:0.5:0.1 (molar ratio). The catalyst was pulverized and formed into 7 to 8-mesh spherical particles, and 60 ml of the particles were packed in a stainless reaction tube. And, a mixture gas containing methanol, phenol and steam ($H_2O$) in a molar ratio of 5:1:1 was fed, together with 10 ml/minute of a nitrogen gas, into the catalyst layer maintained at 330° at a rate of LHSV = 0.6 kg/l.hr. Table 1 shows the results. Further, the above reaction was repeated under the same conditions by using a catalyst containing no germanium dioxide. The results are shown as Comparative Example 1 also in Table 1.

TABLE 1

| | Example 1 $Fe_2O_3—SiO_2—Cr_2O_3—GeO_2—K_2CO_3$ 100 : 2 : 1 : 0.5 : 0.1 (molar ratio) 330° C. | | | Comparative Example 1 $Fe_2O_3—SiO_2—Cr_2O_3—K_2CO_3$ 100 : 2 : 1 : 0.1 (molar ratio) 330° C. | | |
|---|---|---|---|---|---|---|
| Reaction duration time (hrs.) | Phenol reaction ratio (%) | 2,6-Xylenol yield (mol %) | o-Cresol yield (mol %) | Phenol reaction ratio (%) | 2,6-Xylenol yield (mol %) | o-Cresol yield (mol %) |
| 20 | 99.92 | 94.10 | 4.29 | 99.84 | 92.58 | 4.90 |
| 500 | 99.22 | 86.28 | 11.51 | 98.69 | 82.42 | 14.65 |
| 1,000 | 98.68 | 80.30 | 17.08 | 97.93 | 75.69 | 21.10 |
| 1,500 | 98.25 | 75.44 | 21.58 | 96.76 | 65.32 | 31.03 |

EXAMPLE 1 AND COMPARATIVE EXAMPLE 1

12 Kilograms of nonahydrated ferric nitrate and 118.9 g of nonahydrated chromium nitrate were dissolved in 120 liters of purified water, and while the mixture was stirred at room temperature, a dilute solution of 61.3 g of water glass No. 3 ($SiO_2$ content 30%) in 3 liters of water was added. Then, while the mixture was stirred continously, a 10% aqueous ammonia was slowly added dropwise to the mixture. And, when the mixture solution showed pH of 8.0 and when a precipitate was fully formed, the addition of the aqueous ammonia was stopped. And, a suspension of 7.8 g of germanium dioxide in 0.5 liter of purified water was added, and the resultant mixture solution was further stirred continuously for 1 hour to give a precipitate. The precipitate was washed with water, filtered and dried at 120° C. for

EXAMPLES 2-6 AND COMPARATIVE EXAMPLE 2

The same procedure as that of Example 1 was carried out to prepare various catalysts having 7 to 8-mesh spherical particle form but having a different content of germanium dioxide as shown in Table 2.

The same reaction as that described in Example 1 was carried out under the same conditions as those in Example 1 by using the resultant catalysts. Table 2 shows the results obtained after 500 hours' reaction. Further, a catalyst containing no germanium dioxide was prepared in the same way as above, and Table 2 also shows the results of the reaction carried out in the same conditions in the presence of the catalyst containing no germanium dioxide.

TABLE 2

| | Catalyst | Phenol reaction ratio (%) | 2,6-Xylenol yield (mol %) | o-Cresol yield (mol %) | Selectivity to o-position (mol %) |
|---|---|---|---|---|---|
| Example 2 | $Fe_2O_3—SiO_2—Cr_2O_3—GeO_2—K_2CO_3$ 100 : 2 : 1 : 0.3 : 0.1 (molar ratio) | 99.19 | 85.94 | 11.86 | 98.60 |
| Example 3 | $Fe_2O_3—SiO_2—Cr_2O_3—GeO_2—K_2CO_3$ 100 : 2 : 1 : 0.5 : 0.1 | 99.22 | 86.28 | 11.51 | 98.56 |
| Example 4 | $Fe_2O_3—SiO_2—Cr_2O_3—GeO_2—K_2CO_3$ 100 : 2 : 1 : 1.0 : 0.1 (molar ratio) | 99.28 | 86.91 | 10.96 | 98.58 |
| Example 5 | $Fe_2O_3—SiO_2—Cr_2O_3—GeO_2—K_2CO_3$ 100 : 2 : 1 : 2.0 : 0.1 (molar ratio) | 99.33 | 87.53 | 10.38 | 98.57 |

TABLE 2-continued

| | Catalyst | Phenol reaction ratio (%) | 2,6-Xylenol yield (mol %) | o-Cresol yield (mol %) | Selectivity to o-position (mol %) |
|---|---|---|---|---|---|
| Example 6 | $Fe_2O_3$—$SiO_2$—$Cr_2O_3$—$GeO_2$—$K_2CO_3$<br>100 : 2 : 1 : 3.0 : 0.1<br>(molar ratio) | 99.41 | 88.36 | 9.65 | 98.59 |
| Comparative Example 2 | $Fe_2O_3$—$SiO_2$—$Cr_2O_3$—$K_2CO_3$<br>100 : 2 : 1 : 0.1 | 98.69 | 82.42 | 14.65 | 98.36 |

EXAMPLE 7 and COMPARATIVE EXAMPLE 3

The same procedure as that of Example 1 was carried out to prepare a catalyst having 7 to 8-mesh spherical particle form and having an $Fe_2O_3$:$SiO_2$:$Cr_2O_3$:$GeO_2$:$K_2CO_3$ composition of 100:2:1:2:0.1 (molar ratio).

A stainless reaction tube was charged with 60 ml of the catalyst, and a mixture gas containing methanol, phenol and $H_2O$ in a molar ratio of 5:1:1 was fed, together with 10 ml/minute of a nitrogen gas, to the reaction tube at a rate of LHSV=0.6 kg/l·hr. While the reaction temperature was adjusted and maintained such that the yield of 2,6-xylenol became about 80 mol %, the reaction was continued. The catalyst was regenerated at intervals of about 2,000 hours during the reaction. The results are shown in Table 3. Further, a catalyst containing no germanium dioxide was prepared in the same wasy as above. Table 4 shows the results when the same reaction as above was carried out in the presence of the catalyst containing no germanium dioxide (Comparative Example 3).

A stainless reaction tube was charged with 60 ml of the catalyst, and a mixture gas containing methanol, m-cresol and $H_2O$ in a molar ratio of 5:1:1 was fed, together with 10 ml/minute of a nitrogen gas, into the catalyst layer maintained at 322° C. at a rate of LHSV=0.6 kg/l·hr. Table 5 shows the results. Further, a catalyst containing no germanium dioxide was prepared in the same way as above, and the same reaction as above was carried out in the presence of the catalyst (Comparative Example 4). Table 6 shows its results.

TABLE 3

Example 7
Catalyst $Fe_2O_3$—$SiO_2$—$Cr_2O_3$—$GeO_2$—$K_2CO_3$
100 : 2 : 1 : 0.5 : 0.1
(molar ratio)

| Reaction duration time (hrs.) | Reaction temperature (°C.) | Phenol reaction ratio (%) | 2,6-Xylenol yield (mol %) | o-Cresol yield (mol %) | Methanol recovery ratio (mol %) |
|---|---|---|---|---|---|
| 1,000 | 329 | 98.53 | 80.99 | 16.18 | 67.6 |
| 3,000 | 330 | 98.71 | 80.95 | 16.45 | 67.9 |
| 5,000 | 333 | 98.84 | 80.30 | 17.24 | 66.4 |
| 7,000 | 334 | 98.88 | 80.91 | 16.75 | 65.0 |
| 9,000 | 335 | 99.04 | 80.56 | 17.20 | 65.9 |
| 11,000 | 336 | 99.01 | 80.46 | 17.28 | 63.6 |
| 13,000 | 337 | 99.13 | 80.13 | 17.68 | 64.3 |
| 15,000 | 338 | 99.09 | 80.34 | 17.46 | 63.4 |
| 17,000 | 338 | 98.98 | 80.47 | 17.19 | 64.6 |

TABLE 4

Comparative Example 3
Catalyst $Fe_2O_3$—$SiO_2$—$Cr_2O_3$—$K_2CO_3$
100 : 2 : 1 : 0.1
(molar ratio)

| Reaction duration time (hrs.) | Reaction temperature (°C.) | Phenol reaction ratio (%) | 2,6-Xylenol yield (mol %) | o-Cresol yield (mol %) | Methanol recovery ratio (mol %) |
|---|---|---|---|---|---|
| 1,000 | 332 | 98.43 | 80.48 | 16.47 | 60.3 |
| 3,000 | 335 | 98.49 | 80.61 | 16.39 | 64.5 |
| 5,000 | 337 | 99.01 | 80.05 | 17.50 | 63.0 |
| 7,000 | 338 | 99.13 | 80.21 | 17.45 | 55.8 |
| 9,000 | 340 | 99.10 | 80.29 | 17.33 | 51.7 |

EXAMPLE 8 AND COMPARATIVE EXAMPLE 4

The same procedure as that of Example 1 was carried out to prepare a catalyst having 7 to 8-mesh spherical particle form and having an $Fe_2O_3$:$SiO_2$:$Cr_2O_3$:$GeO_2$:$K_2CO_3$ composition of 100:2:1:1:0.1 (molar ratio).

TABLE 5

Example 8
Catalyst $Fe_2O_3$—$SiO_2$—$Cr_2O_3$—$GeO_2$—$K_2CO_3$
100 : 2 : 1 : 1 : 0.1
(molar ratio)
Reaction temperature 322° C.

| Reaction duration time (hrs.) | m-Cresol reaction ratio (%) | 2,3,6-Trimethylphenol yield (mol %) | 2,5-Xylenol yield (mol %) | 2,3-Xylenol yield (mol %) |
|---|---|---|---|---|
| 20 | 99.99 | 92.50 | 4.22 | 0.28 |
| 500 | 99.92 | 90.34 | 6.32 | 0.41 |
| 1,000 | 99.86 | 88.03 | 8.66 | 0.55 |
| 1,500 | 99.76 | 84.71 | 11.99 | 0.79 |

TABLE 6

Comparative Example 4

Catalyst  $Fe_2O_3$—$SiO_2$—$Cr_2O_3$—$K_2CO_3$
100 : 2 : 1 : 0.1
(molar ratio)

Reaction temperature 322° C.

| Reaction duration time (hrs.) | m-Cresol reaction ratio (%) | 2,3,6-Trimethylphenol yield (mol %) | 2,5-Xylenol yield (mol %) | 2,3-Xylenol yield (mol %) |
| --- | --- | --- | --- | --- |
| 20 | 99.95 | 91.70 | 4.75 | 0.36 |
| 500 | 99.86 | 87.83 | 8.74 | 0.55 |
| 1,000 | 99.69 | 83.04 | 13.59 | 1.00 |
| 1,500 | 99.59 | 80.24 | 16.32 | 1.14 |

What is claimed is:

1. A catalyst for alkylation of phenols in the ortho-position with an alcohol, which comprises iron oxide, silica, chromium oxide, germanium oxide and an alkali metal compound.

2. The catalyst of claim 1 wherein the iron oxide, silica, chromium oxide, germanium oxide and alkali metal compound are present in a Fe:Si:Cr:Ge:alkali metal atomic ratio of 100:0.1-20:0.1-5:0.1-10:0.01-5.

3. The catalyst of claim 1 wherein the iron oxide, silica, chromium oxide, germanium oxide and alkali metal compound are present in a Fe:Si:Cr:Ge:alkali metal atomic ratio of 100:0.1-5:0.1-3:0.1-5:0.01-1.

* * * * *